(12) United States Patent
Ponomarev et al.

(10) Patent No.: US 10,151,731 B2
(45) Date of Patent: Dec. 11, 2018

(54) ULTRASONIC SYSTEM FOR NONDESTRUCTIVE TESTING

(71) Applicant: The Boeing Company, Chicago, IL (US)

(72) Inventors: Sergey G. Ponomarev, Lynnwood, WA (US); Wayne Cooper, Seattle, WA (US); Dennis M. Lewis, Seattle, WA (US)

(73) Assignee: The Boeing Comapny, Chicago, IL (US)

( * ) Notice: Subject to any disclaimer, the term of this patent is extended or adjusted under 35 U.S.C. 154(b) by 325 days.

(21) Appl. No.: 14/941,203

(22) Filed: Nov. 13, 2015

(65) Prior Publication Data
US 2017/0138907 A1    May 18, 2017

(51) Int. Cl.
*G01N 29/04* (2006.01)
*G01N 29/34* (2006.01)
(Continued)

(52) U.S. Cl.
CPC ......... *G01N 29/043* (2013.01); *G01N 29/041* (2013.01); *G01N 29/11* (2013.01);
(Continued)

(58) Field of Classification Search
CPC ...... G01N 29/00; G01N 29/04; G01N 29/041; G01N 29/043; G01N 29/032;
(Continued)

(56) References Cited

U.S. PATENT DOCUMENTS 2,573,536 A * 10/1951 Bodine, Jr. ............ F02B 23/08
                                                      123/188.2
4,265,122 A *  5/1981 Cook ................. G01N 29/2418
                                                      367/140
(Continued)

FOREIGN PATENT DOCUMENTS

EP          0 818773           1/1998
EP          1 238 715 A1       9/2002
(Continued)

OTHER PUBLICATIONS

Solodov et al., "Nonlinear air-coupled emission: The signature to reveal and image microdamage in solid materials", Applied Physics Letters, vol. 91, No. 25, Dec. 19, 2007.
(Continued)

*Primary Examiner* — Robert R Raevis
(74) *Attorney, Agent, or Firm* — McDonnell Boehnen Hulbert & Berghoff LLP

(57) ABSTRACT

Example systems and methods for nondestructive ultrasonic testing are provided. One example system includes at least one air-coupled ultrasonic transducer configured to emit primary ultrasound waves that interfere with each other. The primary ultrasound waves include fundamental frequency components that are multiples of each other and emitted simultaneously in locked phase. Further, the interference of the primary ultrasound waves generates a plurality of frequency harmonics in the air. The system also includes at least one receiver configured to receive ultrasonic waves emitted from an object under test.

18 Claims, 15 Drawing Sheets

(51) Int. Cl.
*G01N 29/11* (2006.01)
*G01N 29/46* (2006.01)

(52) U.S. Cl.
CPC ........... *G01N 29/348* (2013.01); *G01N 29/46* (2013.01); *G01N 2291/015* (2013.01); *G01N 2291/02491* (2013.01); *G01N 2291/105* (2013.01)

(58) Field of Classification Search
CPC ...... G01N 29/036; G01N 29/11; G01N 29/12; G01N 29/28; G01N 29/341; G01N 29/343; G01N 29/348; G01N 29/4445; G01N 2291/014; G01N 2291/023; G01N 2291/0289; G01N 2291/105; G01S 7/52038
See application file for complete search history.

(56) References Cited

U.S. PATENT DOCUMENTS

| | | | |
|---|---|---|---|
| 5,679,899 A | | 10/1997 | Webster et al. |
| 5,767,407 A | * | 6/1998 | Sinha .................. G01N 29/036 702/54 |
| 5,824,908 A | | 10/1998 | Schindel et al. |
| 5,889,870 A | | 3/1999 | Norris |
| 6,186,004 B1 | * | 2/2001 | Kaduchak ............ G01N 29/036 73/596 |
| 6,324,912 B1 | * | 12/2001 | Wooh ....................... B61K 9/10 73/629 |
| 6,363,788 B1 | * | 4/2002 | Gorman ............... G01N 17/006 73/597 |
| 6,367,328 B1 | * | 4/2002 | Gorman ............... G01N 17/006 73/290 R |
| 7,839,718 B2 | | 11/2010 | Vu et al. |
| 7,963,165 B2 | | 6/2011 | Sinha |
| 8,151,644 B2 | * | 4/2012 | Brandt ..................... G01H 9/00 73/643 |
| 8,176,783 B2 | * | 5/2012 | Sinha .................. G01N 29/036 73/579 |
| 8,327,709 B2 | * | 12/2012 | Daraio ............... G01N 29/2437 73/632 |
| 8,600,702 B2 | * | 12/2013 | Watts ..................... G01B 17/02 702/171 |
| 9,228,878 B2 | * | 1/2016 | Haw ..................... G01F 23/292 |
| 2010/0000309 A1 | * | 1/2010 | Bierl ....................... F02B 39/16 73/114.77 |
| 2014/0216158 A1 | | 8/2014 | Sanabria Martin et al. |

FOREIGN PATENT DOCUMENTS

| | | | | |
|---|---|---|---|---|
| WO | | WO 00/73781 | 12/2000 | |
| WO | | WO 0073781 A1 | * 12/2000 | ........... G01N 29/036 |

OTHER PUBLICATIONS

Osumi et al., "Basic Study of Non-contact Measurement System for Internal Defect in Solid Materials Using High-Intensity Aerial Ultrasonic Waves", SICE Annual Conference 2012, pp. 1120-1125, Aug. 20, 2012.

Lauterborn et al., "Nonlinear Acoustics in Fluids", Springer Handbook of Acoustics, pp. 265-314, Jan. 1, 2007.

Hati et al., "Phase-Lock Loops in Vibration Environments", 41st Annual Precise Time and Time Interval (PTTI) Meeting, the Institute of Navigation, pp. 303-312, Nov. 19, 2009.

Extended European Search Report prepared by the European Patent Office in application No. EP 16 19 7567, dated Feb. 9, 2017.

Thuras et al., "Extraneous Frequencies Generated in Air Carrying Intense Sound Waves," Bell System Technical Journal, 1935, vol. 14, issue 1, pp. 159-172.

Bigelow, Timothy Allen, Experimental Evaluation of Nonlinear Indices for Ultrasound Transducer Characterizations, Chapter 3: Theoretical analysis of nonlinear absorption, M.S. Thesis, University of Illinois at Urbana—Champaign, 2001, available at http://www.brl.uiuc.edu/Downloads/bigelow/CHAPTER3.PDF.

Croft et al., "Theory, History, and the Advancement of Parametric Loudspeakers: A Technology Overview," American Technology Corporation, 2003.

Galleo-Juarez et al, "Experimental study of nonlinearity in free progressive acoustic waves in air at 20 kHz," Journal de Physique Colloques, 1979, vol. 40, pp. C8-336-C8-340.

Gan et al., "A review of parametric acoustic array in air," Applied Acoustics, 2012, vol. 73, pp. 1211-1219, available at http://dx.doi.org/10.1016/j.apacoust.2012.04.001.

Hillger at al., "Practical Applications of Air—Coupled Ultrasonic Technique," 4th International Symposium on NDT in Aerospace, 2012, available at http://www.ndt.net/article/aero2012/papers/p11.pdf.

Kommareddy, Vamshi K.R., "Air-coupled ultrasonic measurements in composites", Retrospective Theses and Dissertations, Digital Repository at Iowa State University, 2003, Paper 236, available at http://lib.dr.iastate.edu/cgi/viewcontent.cgi?article=1233&context=rtd.

Stößel, Rainer "Air—coupled ultrasound inspection as a new non-destructive testing tool for quality assurance," Dissertation, 2004.

Muhlestein, Michael B, "Analyses of Nonlinearity Measures in High-Amplitude Sound Propagation", Brigham Young University, BYU ScholarsArchive, All Theses and Dissertations, Jul. 8, 2013, Paper 3994, pp. 101-105, available at http://scholarsarchive.byu.edu/cgi/viewcontent.cgi?article=4993&context=etd.

Peters et al., "Non contact inspection of composites using air coupled ultrasound," American Institute of Physics Conference Proceedings, 2003, vol. 22, pp. 973-980.

Solodov et al., "New Opportunities for NDT Using Non-Linear Interactions of Elastic Waves with Defects," Journal of Mechanical Engineering, 2011, vol. 57(3), pp. 169-182.

Solodov et.al., "Classical and non-classical nonlinear effects discerned by airborne ultrasound," Proceedings of 20th International Congress on Acoustics, 2010.

Solodov, Igor, "Nonlinear Acoustic NDT: Approaches, Methods, and Applications," NDT in Progress, 2009, available at http://www.ndt.net/article/Prague2009/ndtip/proceedings/Solodov_10.pdf.

Bhardwaj et al, "High frequency non-contact ultrasonic analysis of materials: introduction and applications," Proceedings of SPIE, Aug. 3, 2001, vol. 4336, p. 117-128.

Lee et al., "Smart cooling technology utilizing acoustic streaming," IEEE Transactions on Components and Packaging Technologies, 2007, vol. 30, issue 4, pp. 691-699.

\* cited by examiner

ULTRASONIC SYSTEM FOR NONDESTRUCTIVE TESTING

FIELD

The present disclosure relates generally to ultrasonic systems and methods for inspecting objects and structures, and more particularly, to ultrasonic systems and methods for nondestructive testing using ultrasonic waves and air-coupled transducers.

BACKGROUND

Ultrasonic testing is a subset of nondestructive testing that involves the propagation of ultrasound waves in an object or material under test. An example ultrasonic system may include an ultrasonic transducer that generates ultrasound waves which are transmitted into an object as the ultrasonic transducer is passed over a surface of the object or near the surface of the object. In a reflection (or pulse-echo) configuration, the ultrasonic transducer may also receive ultrasound waves that are reflected from interfaces and imperfections within the object and then provide the received ultrasound waves to a computing device for analysis. On the other hand, in an attenuation (or through-transmission) configuration, a receiver that is separate from the transducer (e.g., on an opposite side of the object) may receive the ultrasound waves after the ultrasound waves have travelled through the object and then provide the received ultrasound waves to a computing device for analysis.

Within ultrasonic testing, ultrasonic systems may be classified as either liquid-coupled or air-coupled. In liquid-coupled systems, water or another liquid is used as a couplant between the transducer and the surface of the object. Conversely, in air-coupled systems, air or another gas is used as the couplant. Air-coupled systems may thus be considered non-contact systems, since no physical contact between the transducer and the object is required.

In air-coupled systems, a significant amount of the energy of ultrasound waves may be lost due to attenuation in the air. The amount of attenuation in the air is proportional to the frequency of the ultrasound waves. Thus, as the frequency of the ultrasound waves increases, more energy is lost due to attenuation. Furthermore, in some examples, there may be a large difference in acoustic impedances between air and the surface material of an object. This difference in acoustic impedances may also cause a significant loss of energy. For instance, when an ultrasound wave traveling in air impinges on the boundary of solid material, more than 99.9% of the energy of the ultrasound wave may be reflected back due to the mismatch in acoustic impedances. Improvements are therefore desired.

SUMMARY

In one example, an ultrasonic system for nondestructive testing is provided. The ultrasonic system includes at least one air-coupled ultrasonic transducer configured to emit primary ultrasound waves that interfere with each other. The primary ultrasound waves include at least two fundamental frequency components that are multiples of each other and emitted simultaneously in locked phase. Further, the interference of the primary ultrasound waves generates a plurality of frequency harmonics in the air. The ultrasonic system also comprises at least one receiver configured to receive ultrasonic waves emitted from an object under test.

In another example, a method for nondestructive testing is provided. The method includes generating, using at least one air-coupled ultrasonic transducer, a plurality of frequency harmonics in an interference field in the air. The method also includes receiving ultrasonic waves reflected from and generated in an object under test. The ultrasonic waves may be reflected from and generated in the object due to the generating of the plurality of frequency harmonics. And the method includes analyzing, using a computing device, signals indicative of the ultrasonic waves in the time domain, frequency domain, or both to determine at least one property of the object.

In still another example, another method is provided. The method includes generating, using at least one air-coupled ultrasonic transducer, a plurality of frequency harmonics in an interference field in the air. The at least one air-coupled ultrasonic transducer is positioned within a predetermined distance of an air duct. The method also includes receiving ultrasonic waves generated in the air duct. The ultrasonic waves may be generated in the air duct to the generating of the plurality of frequency harmonics. And the method includes analyzing, using a computing device, signals indicative of the ultrasonic waves to determine a flow rate of a fluid through the air duct.

The features, functions, and advantages that have been discussed can be achieved independently in various embodiments or may be combined in yet other embodiments further details of which can be seen with reference to the following description and figures.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying figures, wherein:

DETAILED DESCRIPTION

Figure 1:
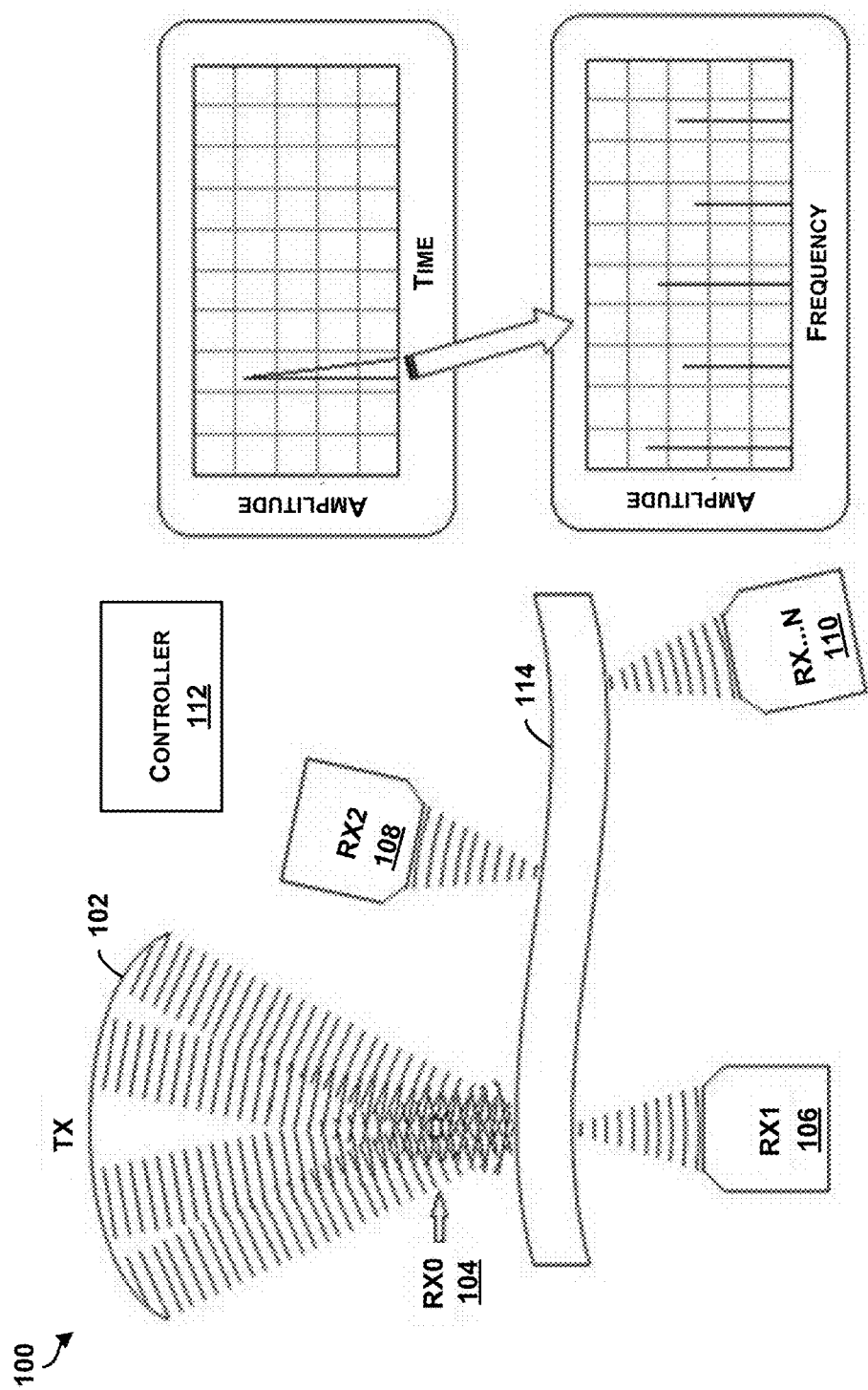
FIG. 1 is a conceptual illustration of an example system according to an example embodiment.

Disclosed embodiments will now be described more fully hereinafter with reference to the accompanying figures, in which some, but not all of the disclosed embodiments are shown. Indeed, several different embodiments may be provided and should not be construed as limited to the embodiments set forth herein. Rather, these embodiments are provided so that this disclosure will be thorough and complete and will fully convey the scope of the disclosure to those skilled in the art.

Within examples, ultrasonic systems and methods for nondestructive testing are provided. In some examples, the systems and methods may facilitate non-contact nondestructive testing and characterization of materials and structures using ultrasound waves and air-coupled transducers. For instance, the systems and methods described herein may enable an inspector to evaluate an object and characterize any defects in the object such as holes or delaminations. Alternatively, the systems and methods described herein may enable an inspector to measure the flow rate of a fluid through a structure such as an air or water duct.

As discussed above, in prior art air-coupled systems, a significant amount of the energy of ultrasound waves may be lost due to attenuation in the air and acoustic impedance mismatches between air and a surface of an object under test. Advantageously, the systems and methods described herein may significantly reduce losses due to attenuation in the air and acoustic impedance mismatches.

In addition, as described herein, the example systems and methods may be used to characterize a variety of properties of complex three-dimensional shapes with better spatial resolution and/or a better signal-to-noise ratio than prior art systems. The example systems and methods may be used to generate simultaneously a well-structured pattern of even and odd harmonics in an entire audio and/or ultrasound region (e.g., from a few Hz to at least 20 MHz). This feature may enable inspecting objects in a shorter time frame as compared to inspecting objects using existing systems. Thus, the example systems and methods may be faster and more cost-effective than existing systems.

In accordance with embodiments disclosed herein, an example system includes at least one air-coupled ultrasonic transducer and at least one receiver. The at least one air-coupled ultrasonic transducer may be configured to emit primary ultrasound waves that interfere with each other. In one example, the at least one air-coupled ultrasonic transducer may emit high power, low frequency ultrasound waves that cause the formation of high frequency harmonics. For instance, the at least one air-coupled ultrasonic transducer may simultaneously emit ultrasound waves at two or more frequencies that are multiples of each other (e.g., a first ultrasound wave at 40 kHz and a second ultrasound wave at 80 kHz). The transmitted ultrasound waves may interfere with each other in the air, and cause the formation of frequency harmonics (e.g., a third harmonic at 120 kHz, a fourth harmonic at 160 kHz, etc.). Thus, emitting the primary ultrasound waves may create a virtual transducer at a distance from the ultrasonic transducer that emits primary ultrasound waves as well as a plurality of frequency harmonics.

When the primary ultrasound waves and the plurality of frequency harmonics reach an object under test, the ultrasound waves and frequency harmonics may excite secondary ultrasound and acoustic waves that are reflected from and generated in the object. These secondary waves may have characteristics that depend on and are indicative of the properties of the object. The secondary waves may be detected by the at least one receiver. In some instances, the at least one receiver may then provide signals indicative of the secondary waves to a controller that is configured to analyze the signals in the time domain and/or frequency domain. The controller may then determine one or more properties of the object using the received signals.

In some instances, the primary ultrasound waves generated by the at least one ultrasonic transducer may form an interference field in which the plurality of frequency harmonics are generated. Further, the interference field may include interference columns with standing wave patterns.

In one embodiment, the at least one ultrasonic transducer may be an array of ultrasonic transducers. In a similar manner, in some embodiments, the at least one receiver may include a set of receivers. For instance, the system may include a first receiver located on a first side of the object in which the at least one ultrasonic transducer is located and a second receiver located on an opposite side of the object.

Various other features of the example systems discussed above, as well as methods for evaluating a surface of an object using these systems, are also described hereinafter with reference to the accompanying figures.

Referring now to the figures, FIG. 1 is a conceptual illustration of an example system 100. As shown in FIG. 1, the example system 100 includes an ultrasonic air-coupled transducer array 102, a plurality of receivers 104, 106, 108, 110, and a controller 112, which may be coupled together by a system bus, network, or other connection mechanism (not shown).

As discussed above, in some examples, the ultrasonic air-coupled transducer array 102 may be replaced by a single ultrasonic transducer. Thus, although the system 100 of FIG. 1 is described as including a transducer array, the example is not meant to be limiting.

In one example, the transducer array 102 may include 300 transducers arranged to emit acoustic and/or ultrasound waves. In one embodiment, the transducer array 102 may be configured to emit primary ultrasound waves that interfere with each other. As an example, each of the transducers of the array may be configured to emit one of two or more fundamental frequency components that are multiples of each other (e.g., 40 kHz and 80 kHz; 50 kHz and 100 kHz, etc.).

Furthermore, each of the fundamental frequency components may be emitted simultaneously in locked phase, such that interference between the primary ultrasound waves generates a plurality of frequency harmonics in the air. The plurality of frequency harmonics may range in frequency from a few hertz to multiple megahertz. The generation of these frequency harmonics can be explained by some of the non-linear effects taking place.

First, it is known that, as a sound wave of high intensity propagates in air, the waveform of the sound wave changes. The distortion of the waveform is caused by the air non-linearity and, as a result, additional frequencies are generated. Sound in air is longitudinal pressure waves that are oscillations of air compression and rarefaction. For a sound of relatively low intensity (typically below sound pressure level ("SPL") of 70 dB), air behaves a linear medium with equal rates of compression and rarefaction. With increasing SPL, air becomes non-linear and the rates of compression and rarefaction vary such that the rates are no longer equal. In particular, the compression portion begins traveling faster than the rarefaction portion. This results in a continuous distortion of the waveform as the wave propagates in air and, as a consequence, in the generation of new, higher frequencies. By way of example, a sine wave becomes more like a sawtooth waveform. The sawtooth waveform contains even and odd harmonics, with the second harmonic being twice the frequency and half the wavelength of the first harmonic, for instance.

Secondly, when at least two high intensity ultrasound waves with different frequencies interfere with each other, their sum frequencies and difference frequencies may be generated because of the non-linearity of the air. This effect is known as the acoustical heterodyning process. Whether different frequencies are generated from two transducers or from a single one, the effect is the same. As an example, if the primary ultrasound waves are 40 kHz and 80 kHz, the interference of the waves, may result in the formation of the difference frequency, 40 kHz, and the sum frequency, 120 kHz, which is the third harmonic. As the power of the primary ultrasound waves increases, $4^{th}$, $5^{th}$, $6^{th}$, and more harmonics may be generated.

The generation of the frequency harmonics using a low frequency (e.g., kilohertz) primary ultrasound wave also contributes to a reduction in losses due to attenuation in the air. The frequency harmonics are generated in an interference field in the air at a point where the primary ultrasound waves are focused rather than emitted by a transducer. As such, the high frequency harmonics do not have to travel through as much air as compared to a scenario in which a transducer emits high frequency waves. And as a result, the high frequency harmonics do not suffer from as much attenuation in the air as if they had been directly emitted by a transducer.

In one example, the primary ultrasound waves may form an interference field that includes interference columns with standing wave patterns. This interference may be measurable by the receiver 104 positioned between the transducer array 102 and an object 114 under test. As discussed further below, in some instances, the standing wave pattern may include alternating regions of air compression and rarefaction, with ultrasound shock waves formed in the regions of compression.

In practice, the primary ultrasound waves emitted by the transducer array 102 as well as the plurality of harmonics generated by the interference of the primary ultrasound waves may propagate throughout the object 114 in a variety of modes, such as longitudinal, shear, surface, and others. The propagation throughout the object 114 may, in turn, generate secondary ultrasound and/or acoustic waves. The plurality of receivers 104, 106, 108, 110 may be configured to receive the secondary ultrasound and/or acoustic waves emitted from the object 114 in various places around the object 114. In some examples, one or more of the plurality of receivers 104, 106, 108, 110 may be air-coupled receivers. The plurality of receivers may, in turn, provide the received signals to the controller 112.

The controller 112 may function to control the transducer array 102. For instance, the controller 112 may energize the transducers of the array to emit ultrasound waves. As another example, the controller 112 may direct and/or focus the transducers of the transducer array to adjust a position of an interference field. The controller 112 may also function to control the plurality of receivers 104, 106, 108, 110 and to process signals received from the plurality of receivers. The plurality of receivers 104, 106, 108, 110 may operate at multiple frequencies simultaneously. Thus, the controller 106 may be configured to process signals received from the plurality of receivers 104, 106, 108, 110 in the time domain, the frequency domain, or both.

In one example, the controller 112 may include one or more processors and one or more memories. For instance, the controller 112 may be a computing device, such as a tablet computing device, laptop computing device, or desktop computing device.

Figure 2:
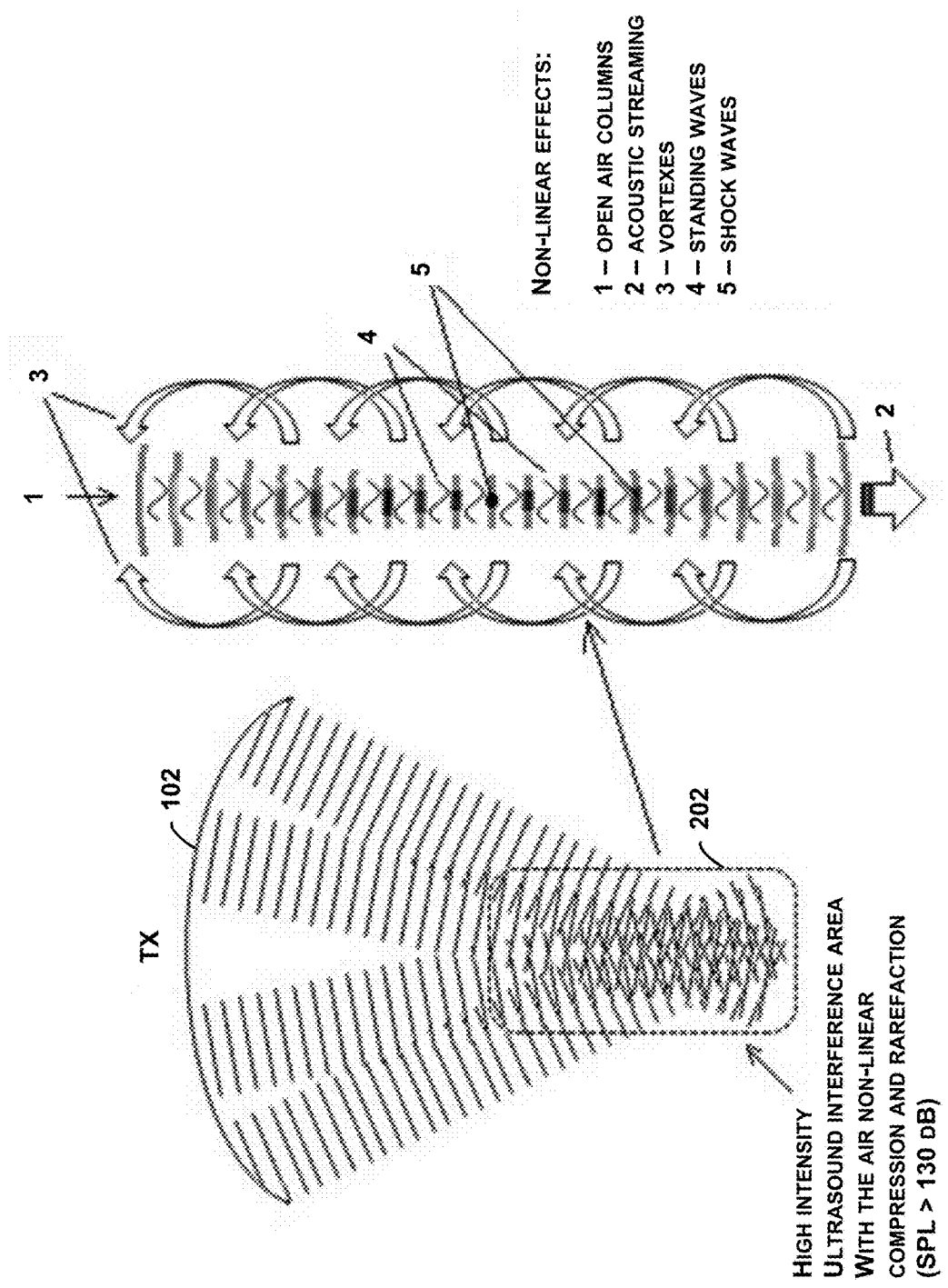
FIG. 2 is a conceptual illustration of an example interference field according to an example embodiment.
Figure 3:
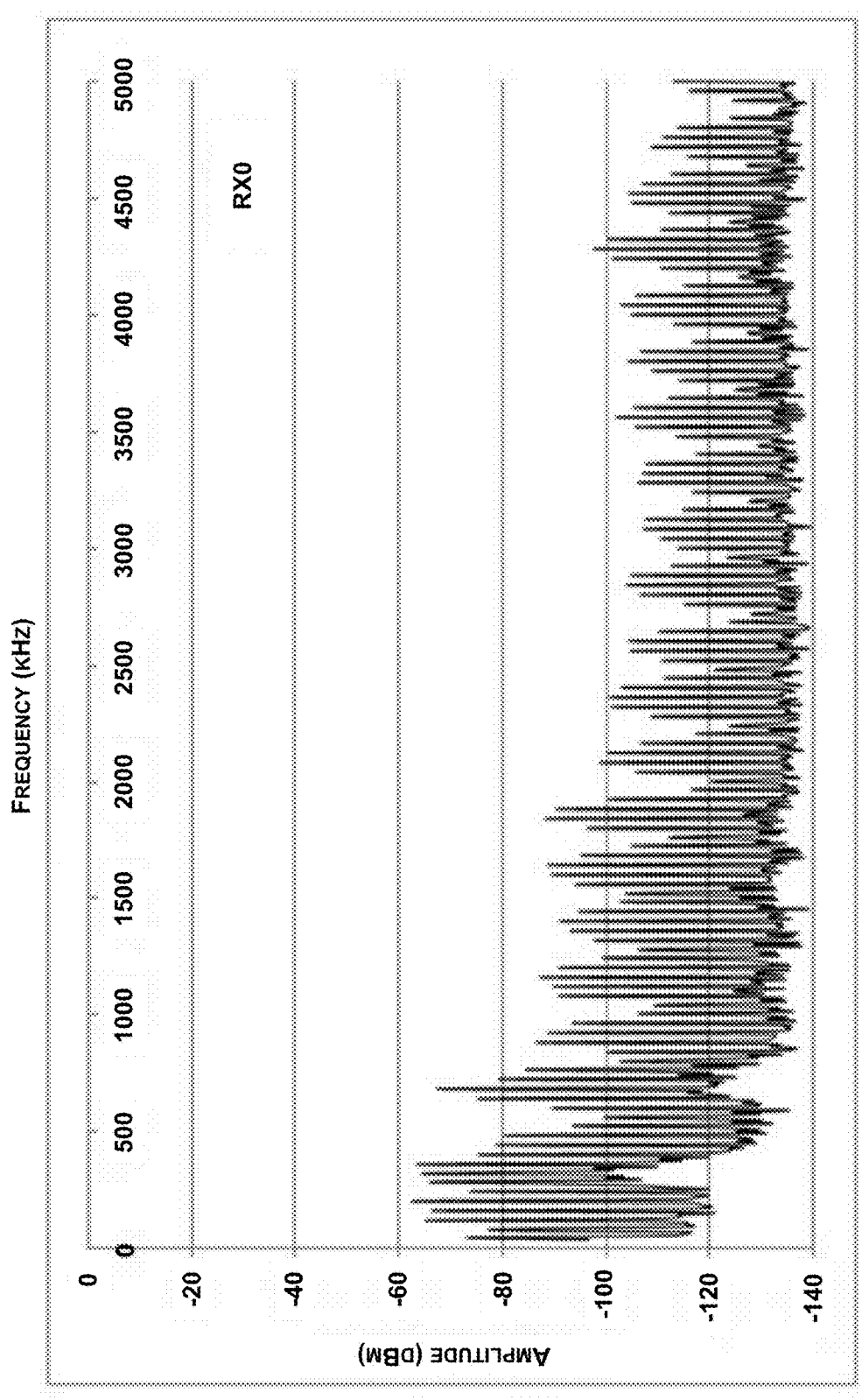
FIGS. 3-6 illustrate example frequency measurements obtained using the example system of FIG. 1.
Figure 4:
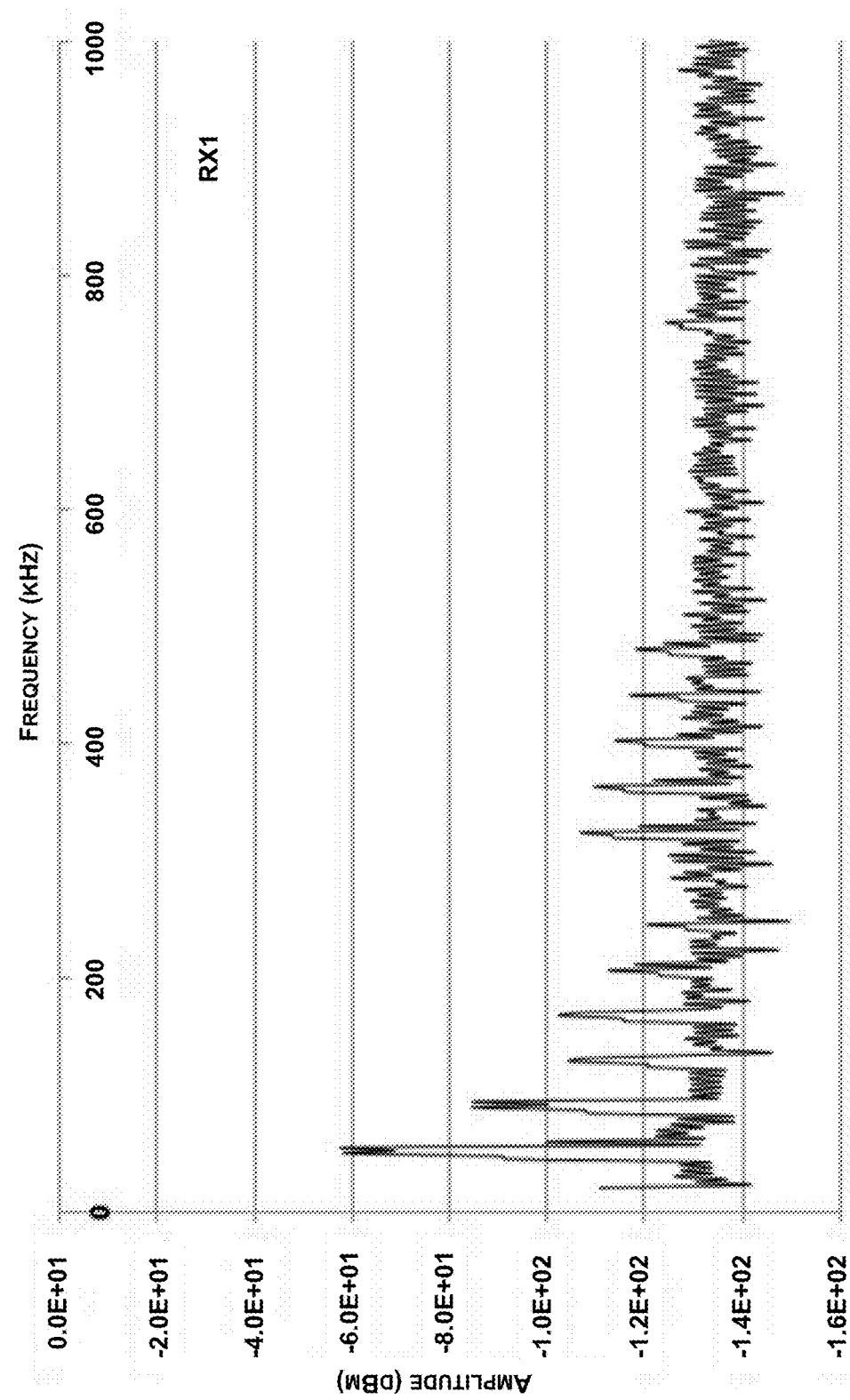
Figure 5:
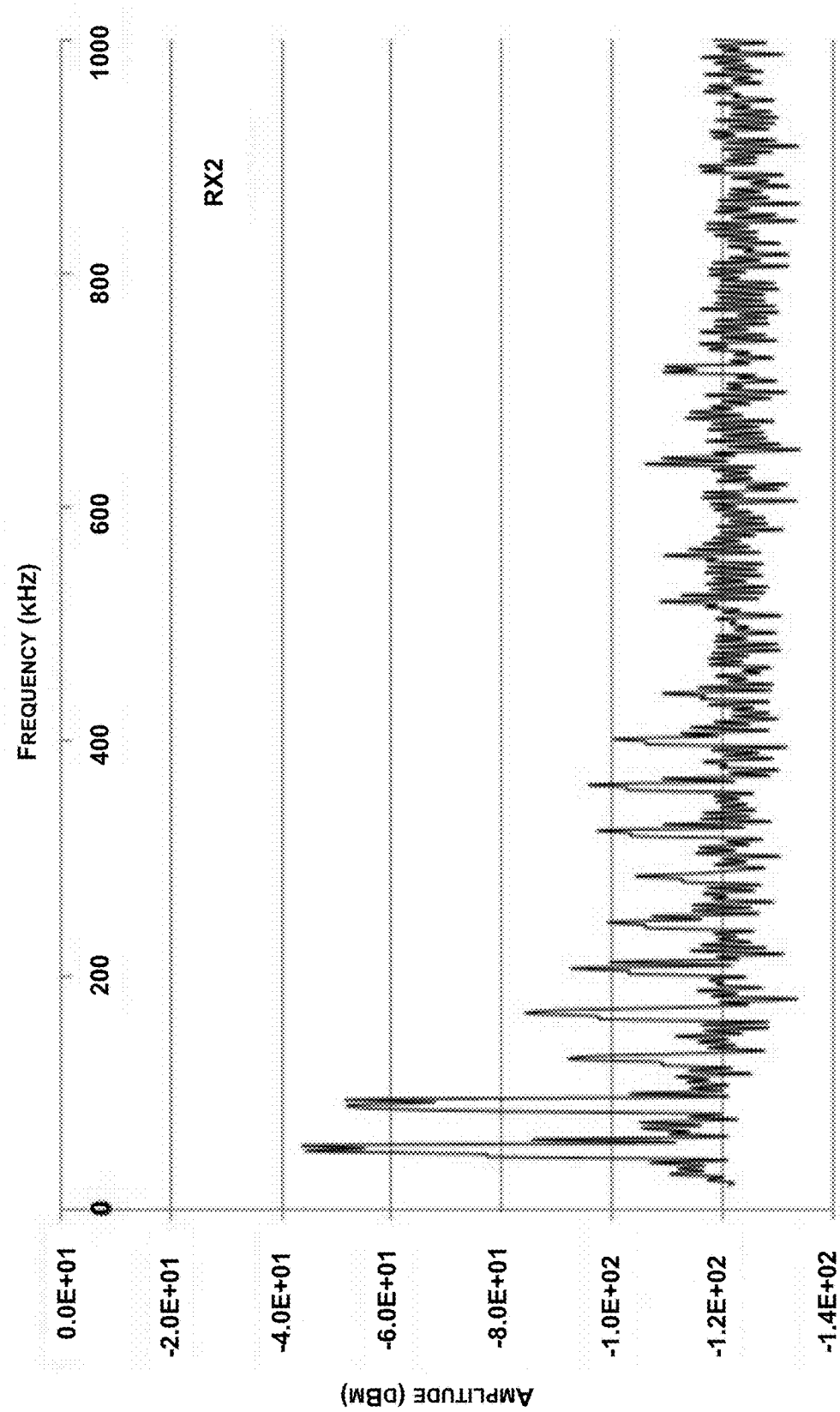
Figure 6:
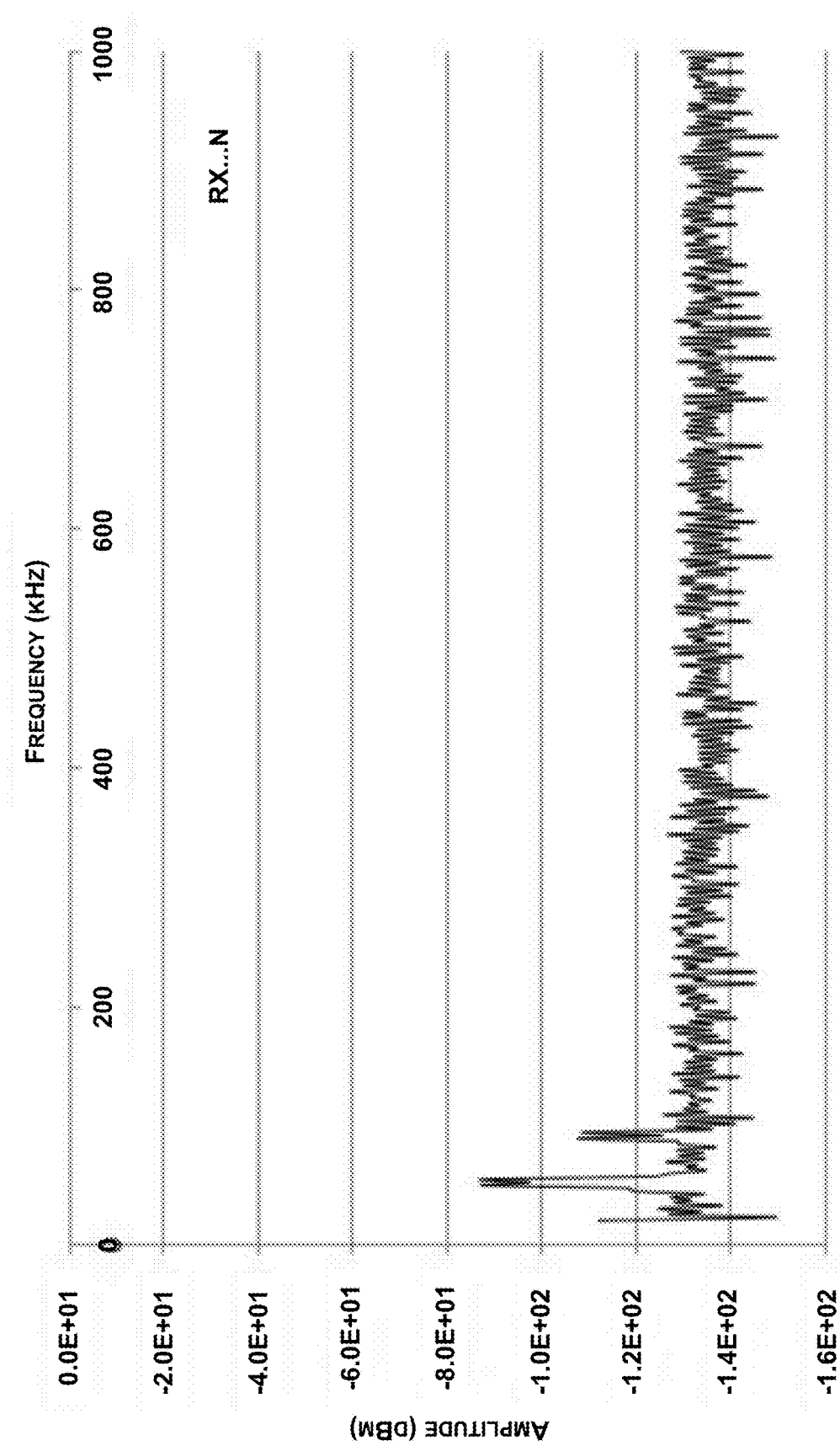

As discussed above, the transducer array 102 may emit primary ultrasound waves that interfere with each other in an interference field. FIG. 2 is a conceptual illustration of an example interference field. In particular, FIG. 2 illustrates non-linear effects that may occur due to interference between primary ultrasound waves emitted by the transducer array 102 of FIG. 1.

As shown in FIG. 2, in one embodiment, the primary ultrasound waves may interfere within an interference area 202. Within the interference area 202, the SPL may be greater than 130 dB. Applicants discovered that by superimposing high power ultrasonic waves having at least two fundamental frequency components that are multiples of each other, structures similar to open air columns with standing waves of multiple frequencies can be formed right in the open air (i.e., acoustic free field). FIG. 2 depicts the formation of such structures within the interference area 202. The structures, referred to herein as interference columns, are similar to open air columns having a pattern of standing waves with alternating regions of air compression and rarefaction.

As also shown in FIG. 2, in some examples, the interference of the primary ultrasound waves in the interference area 202 may generate pronounced and steady airflow directed outward from the transducer. Such airflows are a phenomenon known as acoustic streaming. Acoustic streaming in air is explained as an airflow in the form of vortexes caused by high intensity sound waves.

FIG. 2 also depicts the presence of ultrasound shock waves within the interference area 202. As discussed in more detail below, the presence of the ultrasound shock waves may contribute to the formation of high frequency harmonics in the compression areas within the interference columns.

FIGS. 3-6 illustrate example frequency measurements obtained using the example system 100 of FIG. 1 in an example experiment. In particular, FIGS. 3-6 illustrate example frequency measurements obtained with the receivers 104, 106, 108, 110 of FIG. 1, respectively. In the experiment, the transducer array 102 included 300 40-kHz air-coupled transducers and was measured to produce a SPL of about 145 dB. The transducer array 102 was focused on the center of a carbon composite panel at a focus length of six inches. The carbon fiber panel was approximately 5 feet by 5 feet. The receivers 104, 106, 108, 110 were placed around the carbon fiber composite panel. Specifically, receiver 104 was positioned in the interference field, facing the panel, at a distance of two inches from the panel; receiver 106 was positioned on the back side of the panel; receiver 108 was positioned on the front side of the panel at approximately one foot away from the interference field; and receiver 110 was positioned on the back side of the panel in an upper corner. The frequency measurements shown in FIG. 3, for example, indicate the presence of even and odd harmonics with frequencies as high as a few megahertz.

Figure 7:
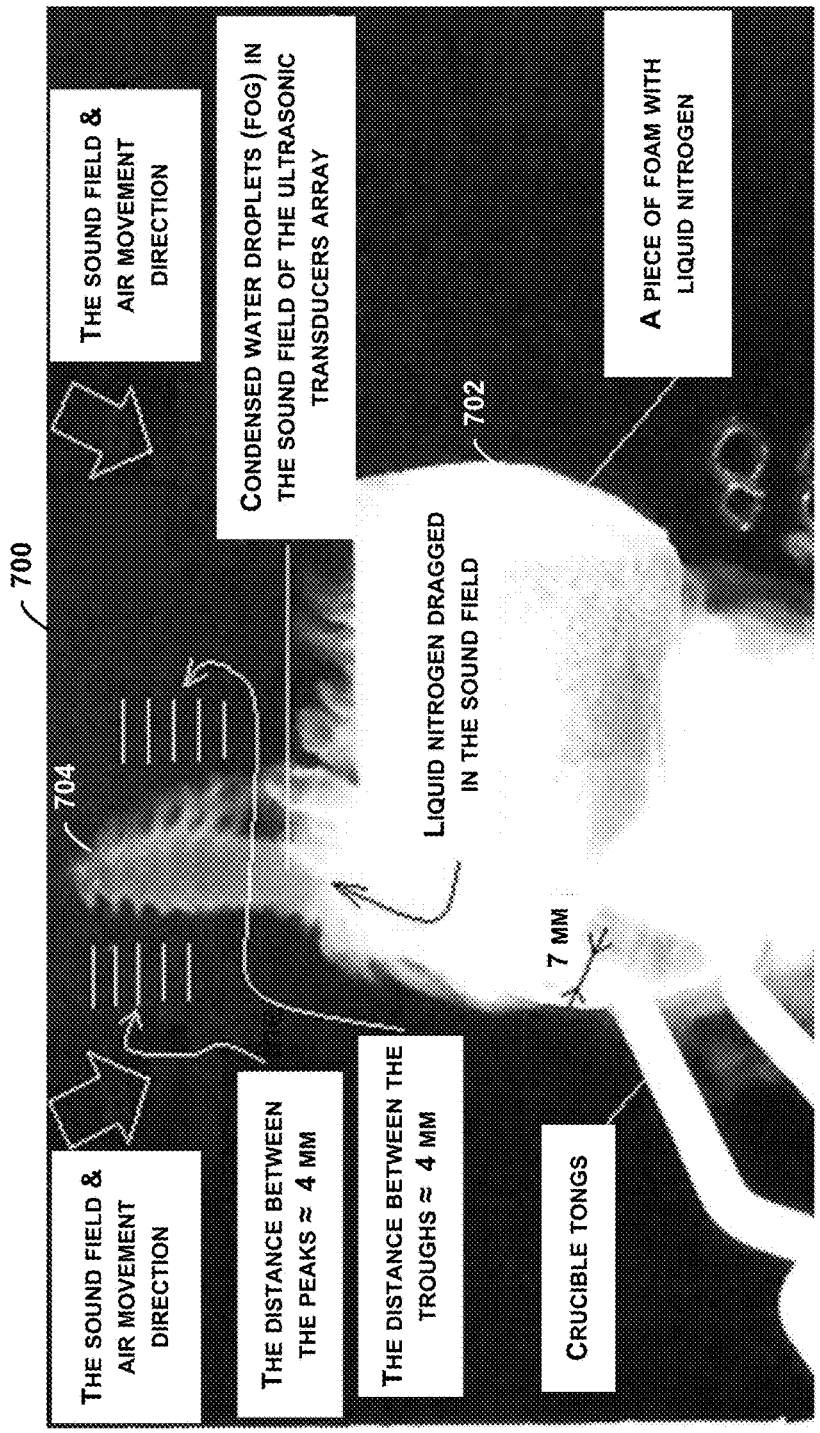
FIG. 7 illustrates example interference columns according to an example embodiment.

FIG. 7 illustrates example interference columns. In particular, FIG. 7 is an image 700 of interference columns visualized with liquid nitrogen during an experiment. In the experiment, a piece of foam 702 loaded with liquid nitrogen was placed within the focus of a transducer array having 300 transducers (not shown). The fundamental frequency of the transducer array was measured to be about 42.363 kHz. Within the focus, the SPL was about 130 dB. At this SPL, the transducer array generated airflow directed outward from the transmitter array and in the form of vortexes. The airflow was measured to have a velocity of about 1.3 meters per second.

As shown in the image 700, during the experiment, the liquid nitrogen cooled the air, producing a fog 704. Fog forms when the difference between the air temperature and the dew point is less than 4° F. At the time of the experiment, the room air temperature was about 73° F. and the relative humidity was about 45%. These conditions correspond to a dew point of 50° F. and a fog formation temperature of about 54° F.

The fog 704 highlighted and revealed the interference columns by flowing into the interference columns. Peaks and troughs of the interference columns are visible in the image 700 due to the differences in the dew points in the neighboring areas. Based on image analysis of the image 700, the distances between the peaks and troughs of the fog 704 appeared to be equal and about 4 mm. The 4-mm distance is about one half wavelength of a 40 kHz ultrasound in air. In particular, the 4-mm distance corresponds to the ultrasound frequency of 42.368 kHz which is in good agreement with the measured frequency of the transducer array's first harmonic during the experiment, 42.363 kHz. Furthermore, the fog 704 was observed to be actually dragged into the interference columns, indicating the existence of areas of negative pressure as well as downstream and upstream vortexes in the airflow generated by the transducer array.

Figure 8:
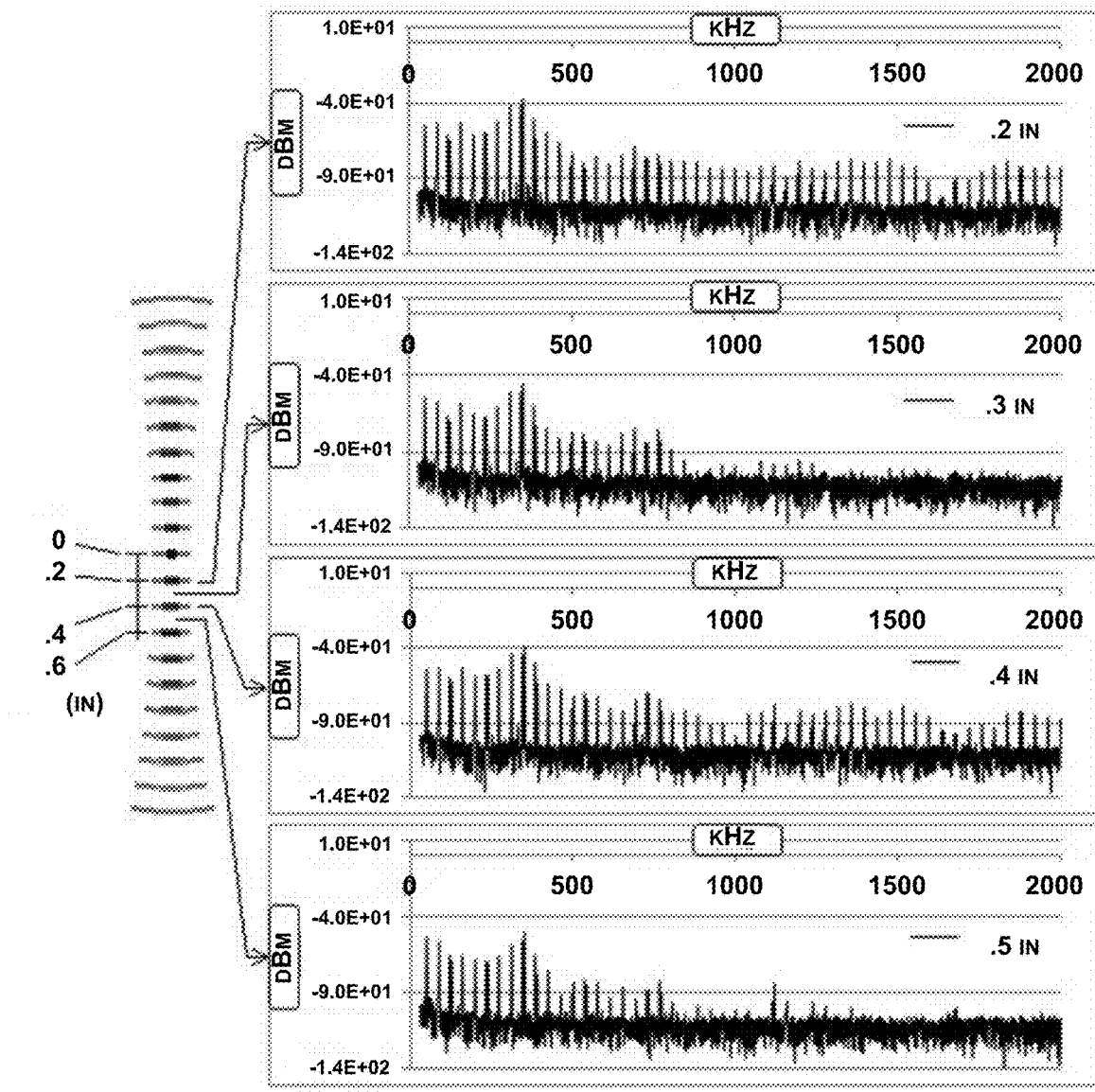
FIG. 8 illustrates example frequency measurements indicative of a plurality of frequency harmonics according to an example embodiment.

FIG. 8 illustrates example frequency measurements indicative of a plurality of frequency harmonics. In particular, FIG. 8 illustrates frequency harmonics measured in another experiment. During the experiment, a transducer array having 300 transducers emitted primary ultrasound waves. The primary ultrasound waves had frequencies of either approximately 40 kHz or 80 kHz. Frequency measurements were done with a 300 kHz receiver initially placed in the focus of the transducer array and then moved further away from the transducer array in 0.1-inch increments.

As shown in FIG. 8, the receiver detected different numbers of harmonics in the areas of air compression and rarefaction. Specifically, in the areas of rarefaction (i.e., 0.3 inches and 0.5 inches in FIG. 8), the received detected harmonics up to 1 MHz. On the other hand, in the areas of compression (i.e., 0.2 inches and 0.4 inches in FIG. 8), the receiver detected harmonics up to 1 MHz as well as harmonics above 1 MHz. The average distance between the compression and rarefaction areas appeared to be within 0.16-0.20 inches. This same distance was measured and visualized with liquid nitrogen in the experiment described above with respect to FIG. 7.

Figure 9:
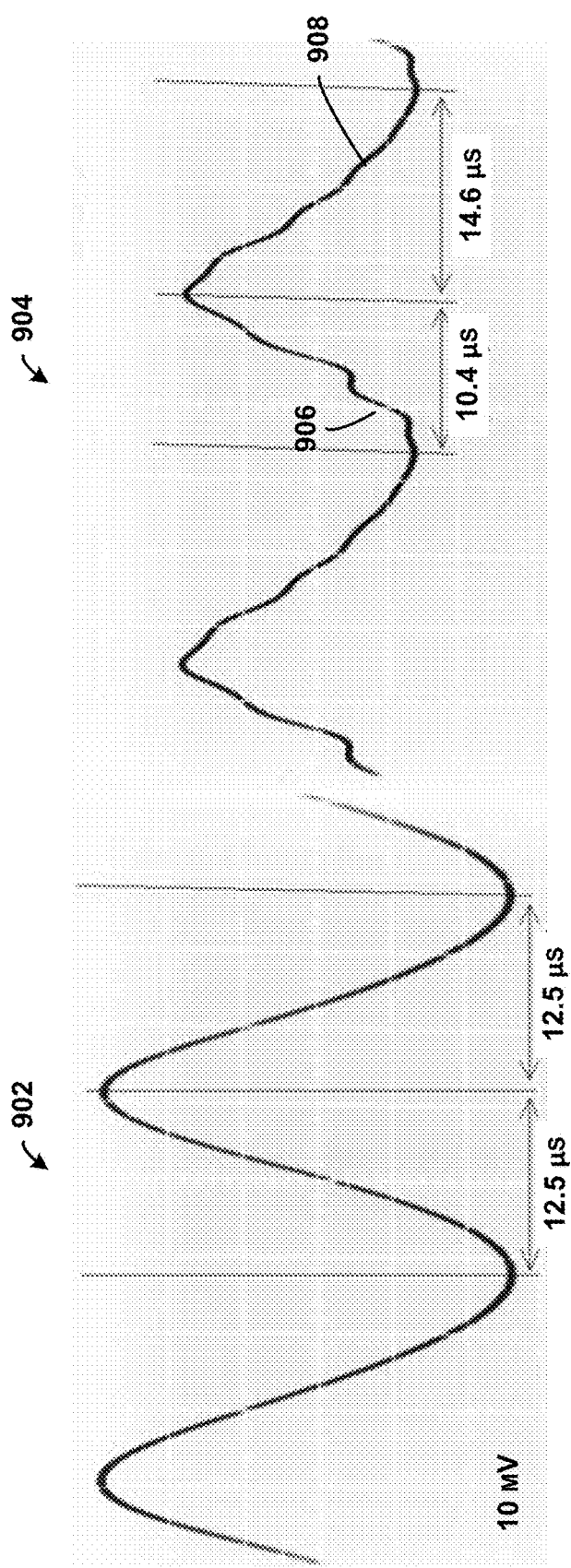
FIG. 9 illustrates example oscillograms of an interference field according to an example embodiment.

As discussed above, the generation of the higher MHz harmonic in the air compression areas is believed to be caused by the formation of shock waves. FIG. 9 illustrates example oscillograms 902, 904 of an interference field measured with a receiver placed in a focus of a transducer array having 300 transducers.

The left oscillogram 902 shows the ultrasound waveform when 9 watts are supplied to the transducer array (low power). At this power, the transducer array may generate harmonics below 500 kHz without generating any higher harmonics.

The right oscillogram 904 shows the ultrasound waveform when 82 watts are supplied to the transducer array (high power). The right oscillogram 904 shows the sequence of one half wavelength of rarefaction, then one half wavelength of compression, then another half wavelength of rarefaction. At low power, the waveform is symmetrical with the total time sum equal to 25 microseconds which corresponds to a frequency of 40 kHz. Whereas, at high power, the sequence becomes unsymmetrical, with a 2-microsecond steeper front 906 of the waveform and a 2-microsecond longer and gradual back 908 of the waveform. Such a transformation of the waveform between low power and high power is indicative of the formation of shock waves.

Figure 10:
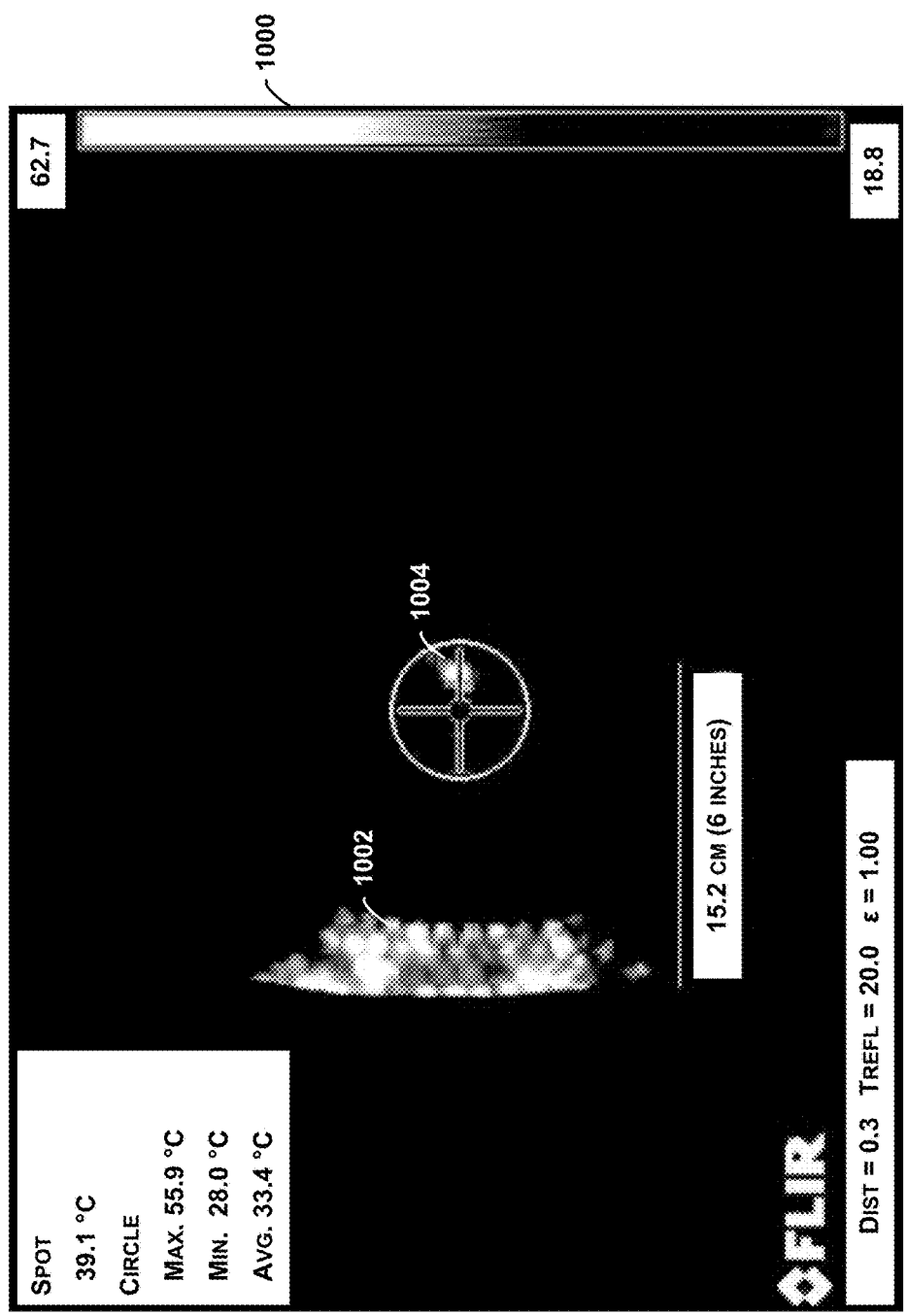
FIG. 10 illustrates an infrared image of an ultrasonic transducer array and its focus point according to an example embodiment.

FIG. 10 illustrates an infrared image 1000 of an ultrasonic transducer array 1002 and its focus point 1004 during an example experiment. As discussed above, the interference field generated by the transducer 1002 may create a temperature gradient. In the example experiment, the ultrasonic transducer 1002 was a transducer array having 300 transducers. The infrared image 1000 was taken with a black piece of foam as the background. As shown in FIG. 10, the maximum temperature of the focus point was measured to be about 56° C. The increase in temperature at the focus point is indicative of the formation of ultrasound shock waves in the compression areas of the interference field.

Advantageously, the formation of ultrasound shock waves contributes to a reduction in losses due to acoustic impedance mismatches between the air and a surface of an object. Shock waves change the properties of air dramatically, and the air essentially becomes a quasiliquid where the shock waves are formed. This quasiliquid may be in contact with a surface of an object under test and may have an acoustic impedance that is greater than the acoustic impedance of air. In other words, the acoustic impedance mismatch between the quasiliquid and a solid may be less than the acoustic impedance mismatch between air and a solid. As a result, when shock waves are present, ultrasound waves directed towards an object under test cross a quasiliquid to solid boundary, rather than crossing an air to solid boundary, and a lesser amount of the energy of the ultrasound waves is reflected back towards the transducer.

Figure 11:
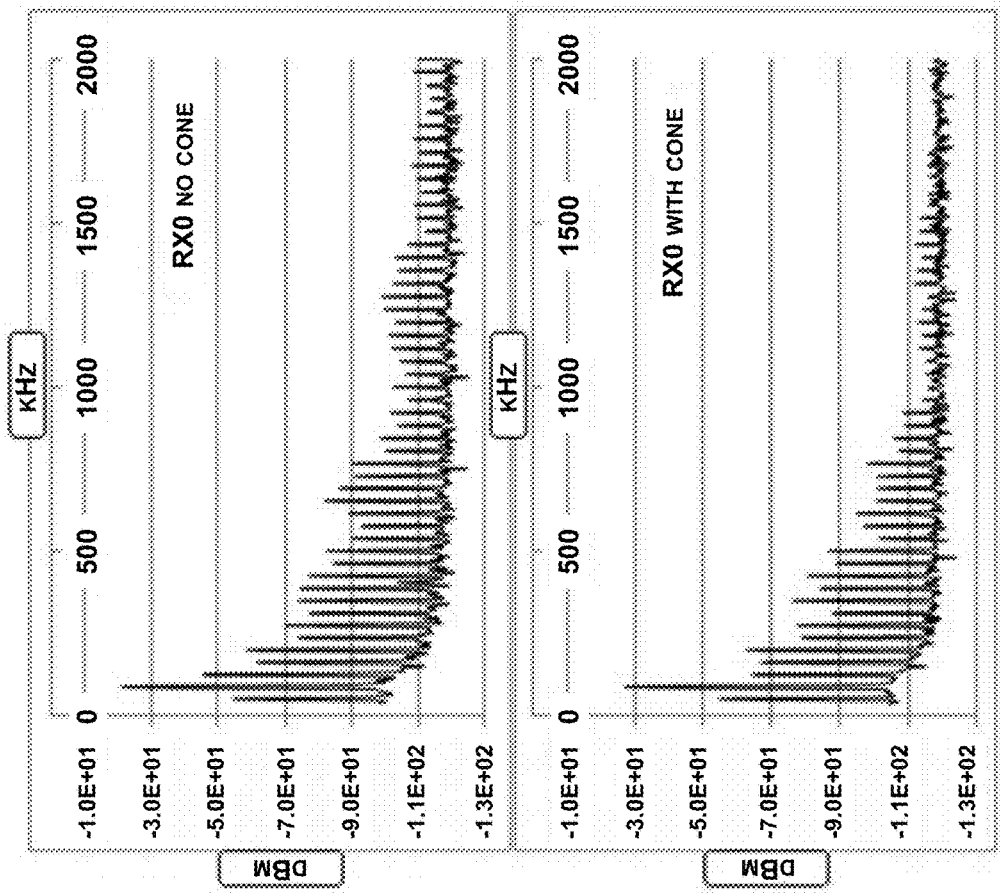
FIG. 11 is a conceptual illustration of an inspection of an object according to an example embodiment.
Figure 11:
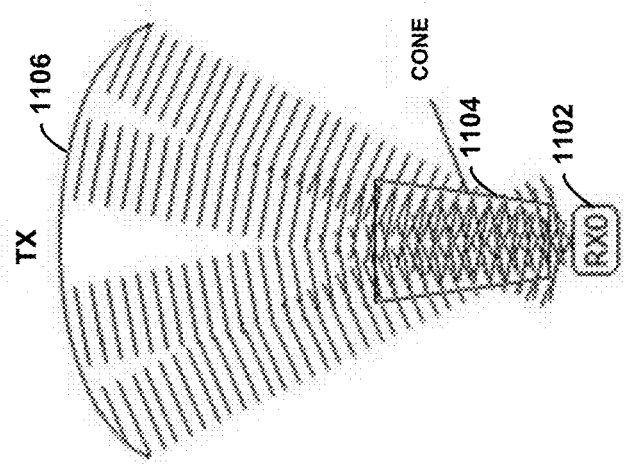

FIG. 11 is a conceptual illustration of an inspection of an object according to an example embodiment. In particular, FIG. 11 shows changes in the frequencies measured by a receiver 1102 when a plastic cone 1104 is placed in close proximity to the focus point of a transducer array 1106. Without the plastic cone 1104 near the focus point of the transducer array 1106, the receiver 1102 detects a plurality of frequency harmonics, including frequency harmonics in the megahertz range. When the plastic cone 1104 is placed near the focus point of the transducer array 1106, the plastic cone 1104 changes the characteristics of the plurality of frequency harmonics. For example, the received power of some of the frequency harmonics is reduced due to the presence of the plastic cone 1104. In some examples, the receiver 1102 may be configured to provide the signals received with and without the plastic cone 1104 to a controller (not shown). In this manner, the controller may determine one or more properties of the plastic cone by analyzing the received signals.

Figure 12:
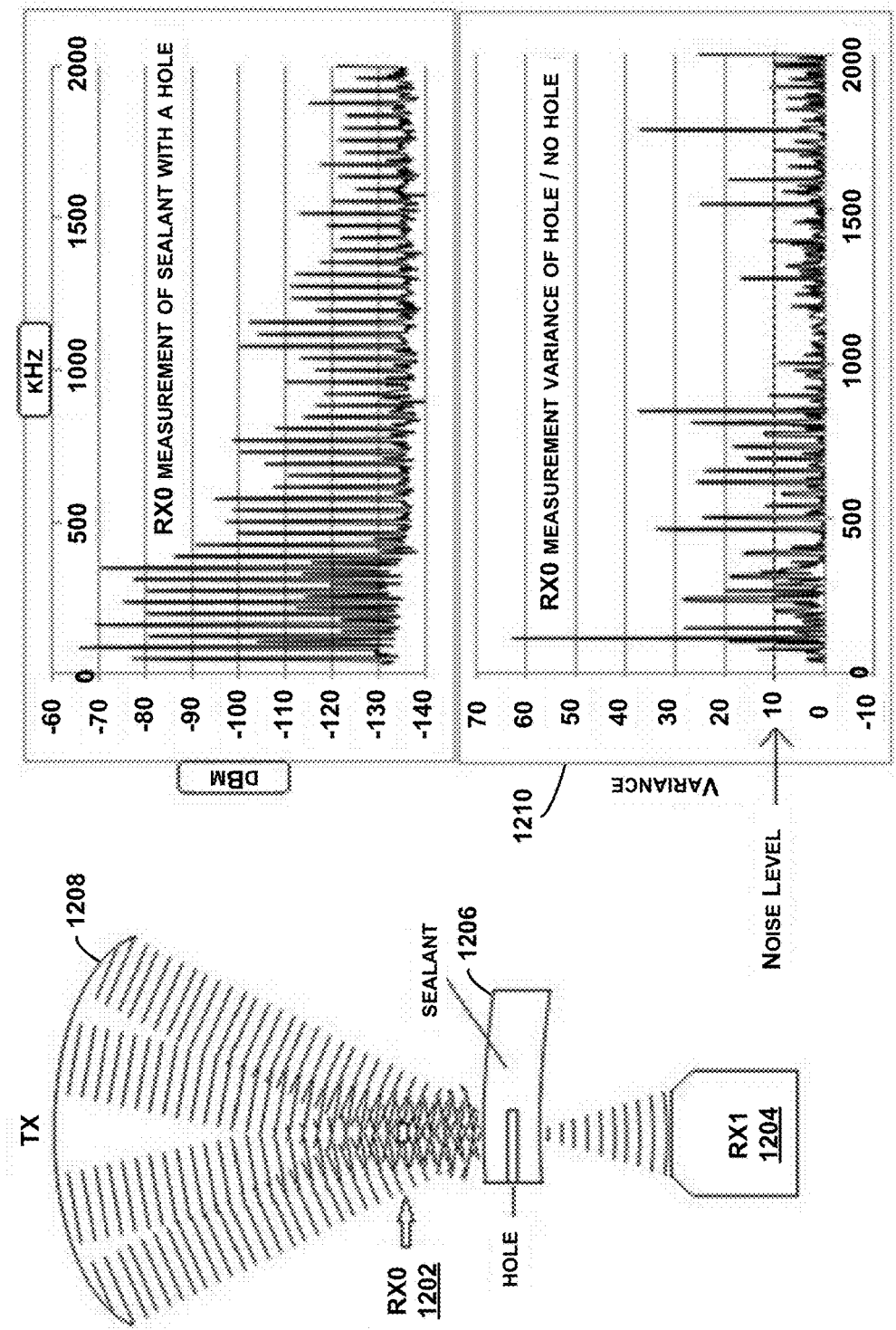
FIGS. 12 and 13 are conceptual illustrations of an inspection of another object according to an example embodiment.
Figure 13:
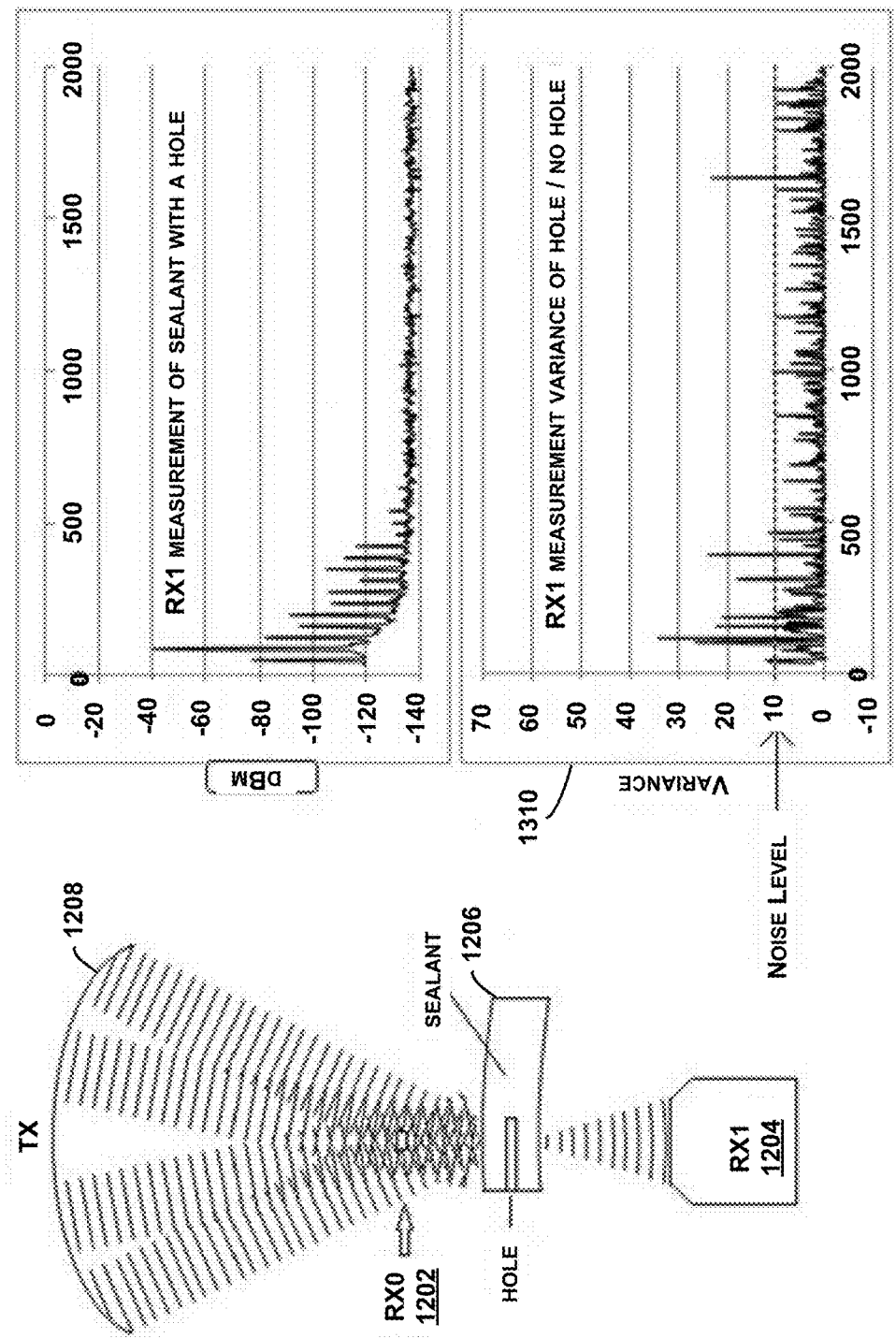

FIGS. 12 and 13 are conceptual illustrations of an inspection of another object according to an example embodiment. In particular, FIGS. 12 and 13 show changes in the frequencies measured by receivers 1202 and 1204, respectively, which are indicative of the presence of a hole in a sample of polysulfide sealant 1206. In order to obtain the frequency measurements presented in FIGS. 12 and 13, the receivers 1202 and 1204 first measured ultrasound signals emitted from the sample of polysulfide sealant 1206 without a hole in the sample as a transducer array 1208 emitted primary ultrasound waves. Subsequently, a hole was added to the sample of polysulfide sealant 1206, and additional frequency measurements were obtained using the receivers 1202 and 1204.

In FIG. 12, and in particular in a graph 1210, the difference (i.e., variance) between the frequency measurements obtained by the receiver 1202 with and without the hole in the sample of the polysulfide sealant 1206 is shown. As indicated in the graph 1210, there are noticeable changes in the frequency measurements obtained by the receiver 1202 with and without the hole in the sample of the polysulfide sealant 1206. The results depicted in the graph 1210 demonstrate that a controller or an operator may analyze frequency measurements determined using the receiver 1202 to determine that a sample has a hole.

Similarly, in a graph 1310 of FIG. 13, the difference (i.e., variance) between the frequency measurements obtained by the receiver 1204 with and without the hole in the sample of the polysulfide sealant 1206 is shown. As indicated in the graph 1310, there are noticeable changes in the frequency measurements obtained by the receiver 1202 with and without the hole in the sample of the polysulfide sealant 1206. The results depicted in the graph 1310 demonstrate that a controller or an operator may analyze frequency measurements determined using the receiver 1204 to determine that a sample has a hole.

Figure 14:
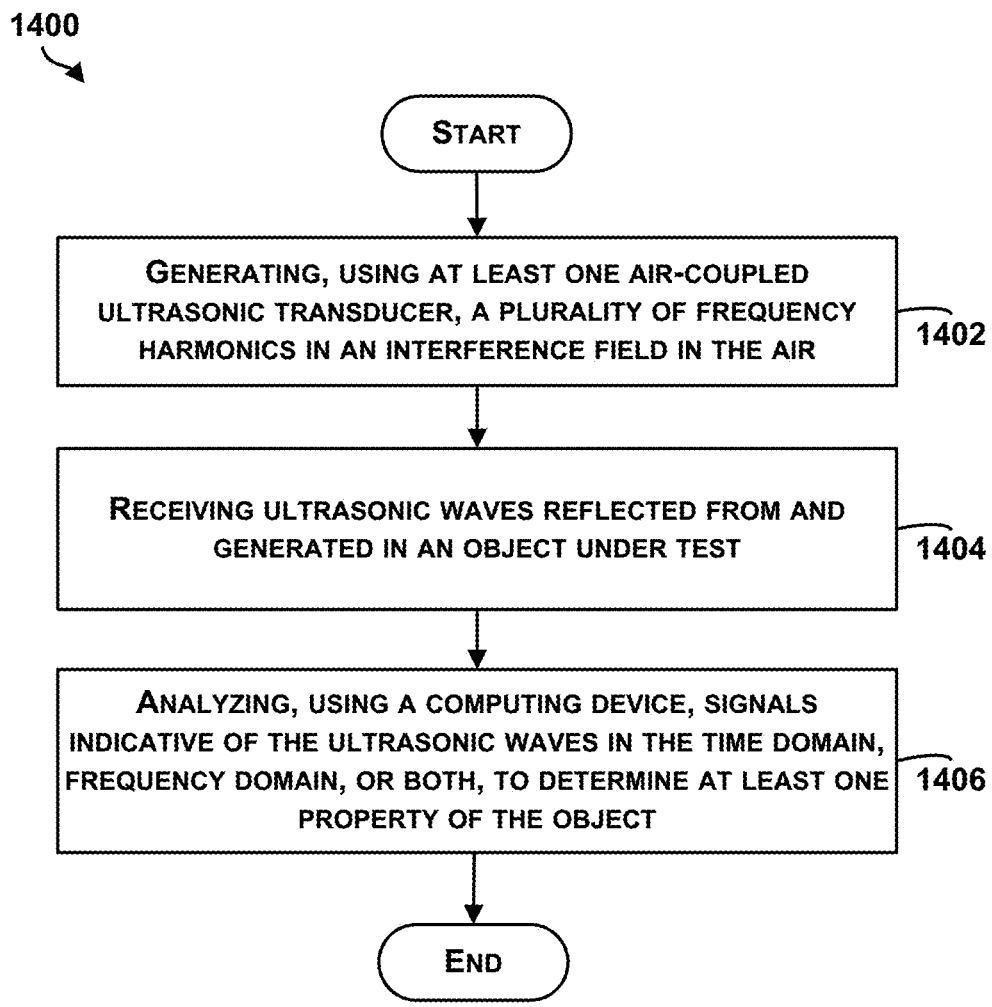
FIG. 14 is a flowchart of an example method for nondestructive testing according to an example embodiment.

FIG. 14 is a flowchart of an example method for nondestructive testing according to an example embodiment. Method 1400 shown in FIG. 14 present an embodiment of a method that could be used with the system shown in FIG. 1, for example, or any of the systems disclosed herein. Example devices or systems may be used or configured to perform logical functions presented in FIG. 14. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions. Method 1400 may include one or more operations, functions, or actions as illustrated by one or more of blocks 1402-1406. Although these blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. The computer readable medium may include non-transitory computer readable medium or memory, for example, such as computer readable media that stores data for short periods of time like register memory, processor cache, and RAM. The computer readable media may also be any other volatile or non-volatile storage systems. The computer readable medium may be considered a tangible computer readable storage medium, for example.

In addition, each block in FIG. 14 may represent circuitry that is wired to perform the specific logical functions in the process. Alternative implementations are included within the scope of the example embodiments of the present disclosure in which functions may be executed out of order from that shown or discussed, including substantially concurrent or in reverse order, depending on the functionality involved, as would be understood by those skilled in the art.

Initially, at block 1402, the method 1400 includes generating, using at least one air-coupled ultrasonic transducer, a plurality of frequency harmonics in an interference field in the air. By way of example, a controller may cause a transducer array to emit primary ultrasound waves that interfere with each other in the air. The primary ultrasound waves may include frequency components that are multiples of each other, and the primary ultrasound waves may be emitted simultaneously. When the primary ultrasound waves interfere with each other, the primary ultrasound waves may generate a plurality of frequency harmonics.

In some examples, the controller may also adjust a position of the interference field. In one example, adjusting the position of the interference field may involve directing (e.g., electronically or mechanically steering) the primary ultrasound waves emitted by the ultrasonic transducer. Additionally or alternatively, adjusting the position of the interference field may involve focusing the ultrasonic transducer on the surface of an object under test. In some examples, an operator or a robotic system may position the at least one air-coupled ultrasonic transducer within a predetermined distance of the object. For instance, the operator or robotic system may move the transducer such that it is focused on the surface of the object under test.

At block 1404, the method 1400 includes receiving ultrasonic waves reflected from and generated in an object under test. By way of example, a non-contact air-coupled ultrasonic receiver may receive the ultrasonic waves. In line with the discussion above, the ultrasonic waves may be reflected from and generated in the object under test due to the generating of the plurality of frequency harmonics. For instance, the plurality of frequency harmonics may excite ultrasonic waves that are reflected from and generated in the object. The ultrasonic receiver may be located on a same side of the object as the at least one transducer or an opposite side of the object.

At block 1406, the method 1400 includes analyzing, using a computing device, signals indicative of the ultrasonic waves in the time domain, frequency domain, or both, to determine at least one property of the object. As one example, the computing device may analyze the signals to determine whether the object includes a hole, indentation, or internal deformation (e.g., a delamination).

Figure 15:
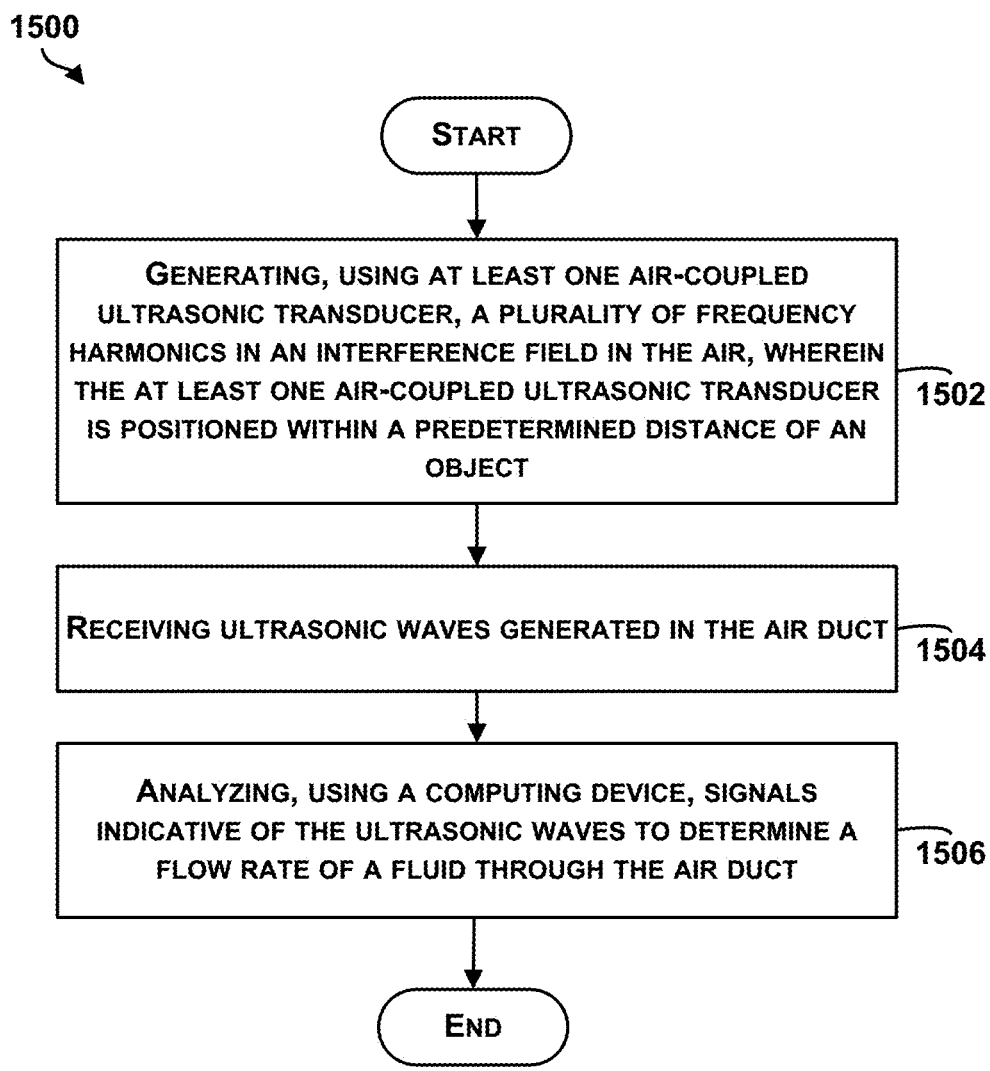
FIG. 15 is a flowchart of another example method for nondestructive testing according to an example embodiment.

FIG. 15 is a flowchart of another example method for nondestructive testing according to an example embodiment. Method 1500 shown in FIG. 15 present an embodiment of a method that could be used with the system 100 shown in FIG. 1, for example, or any of the systems disclosed herein.

Method 1500 may include one or more operations, functions, or actions as illustrated by blocks 1502-1506 of the flowchart. Although the blocks are illustrated in a sequential order, these blocks may also be performed in parallel, and/or in a different order than those described herein. Also, the various blocks may be combined into fewer blocks, divided into additional blocks, and/or removed from the flowchart, based upon the desired implementation of the method 1500. Each block may represent a module, segment, or a portion of program code, which includes one or more instructions executable by a processor for implementing specific logical functions or steps in the process. In addition, each block in FIG. 15 may represent circuitry that is wired to perform the specific logical functions in the process.

Initially, at block 1502, the method 1500 includes generating, using at least one air-coupled ultrasonic transducer, a plurality of frequency harmonics in an interference field in the air. The at least one air-coupled ultrasonic transducer may be positioned within a predetermined distance of an air duct, such as an air duct of an aircraft structure. In one example, a controller may cause a transducer array to emit primary ultrasound waves that interfere with each other in the air. The primary ultrasound waves may include frequency components that are multiples of each other, and the primary ultrasound waves may be emitted simultaneously. When the primary ultrasound waves interfere with each other, the primary ultrasound waves may generate a plurality of frequency harmonics.

At block 1504, the method 1500 includes responsive to the generating, receiving ultrasonic waves generated in the air duct. By way of example, a non-contact air-coupled ultrasonic receiver may receive the ultrasonic waves. In line with the discussion above, the ultrasonic waves may be generated in the air duct due to the generating of the plurality of frequency harmonics. The ultrasonic receiver may be located on a same side of the object as the at least one transducer or an opposite side of the object.

At block 1506, the method 1500 includes analyzing, using a computing device, signals indicative of the ultrasonic waves to determine a flow rate of a fluid through the air duct. In one example, the controller may measure Doppler shifts of multiple frequencies to determine the flow rate. For instance, the controller may measure Doppler shifts in wavelengths of reflections from particles moving within the air duct. In this manner, the flow rate through the air duct may be estimated without removing the air duct and installing a flow meter.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An ultrasonic system for nondestructive testing, comprising:
   an array of air-coupled ultrasonic transducers configured to emit primary ultrasound waves that: interfere with each other, generate a plurality of frequency harmonics in the air, and form ultrasound shock waves that modify an acoustic impedance of the air, wherein the primary ultrasound waves comprise at least two fundamental frequency components that are multiples of each other and emitted simultaneously in locked phase; and
   at least one receiver configured to receive ultrasonic waves emitted from an object under test.

2. The ultrasonic system of claim 1, wherein the primary ultrasound waves form an interference field, and wherein the plurality of frequency harmonics is generated in the interference field.

3. The ultrasonic system of claim 2, wherein the interference field comprises interference columns with standing wave patterns generated in the air.

4. The ultrasonic system of claim 3, wherein the standing wave patterns comprise alternating regions of air compression and rarefaction, and wherein the ultrasound shock waves are formed in the regions of compression.

5. The ultrasonic system of claim 1, wherein the plurality of frequency harmonics comprise frequencies between 20 Hz and 20 MHz.

6. The ultrasonic system of claim 1, wherein the at least two fundamental frequency components are below 100 kHz.

7. The ultrasonic system of claim 1, wherein the at least one receiver comprises a non-contact air-coupled receiver.

8. The ultrasonic system of claim 7, wherein the at least one receiver is configured to receive ultrasonic waves reflected from and generated in the object.

9. The ultrasonic system of claim 1, further comprising a controller,
   wherein the at least one receiver is further configured to provide signals indicative of the received ultrasonic waves to the controller, and
   wherein the controller is configured to analyze the signals in the time domain, frequency domain, or both.

10. An ultrasonic system for nondestructive testing, comprising:
    at least one air-coupled ultrasonic transducer configured to emit primary ultrasound waves that: interfere with each other, generate a plurality of frequency harmonics in the air, and form ultrasound shock waves that modify an acoustic impedance of the air, wherein the primary ultrasound waves comprise at least two fundamental frequency components that are multiples of each other and emitted simultaneously in locked phase; and
    at least one receiver configured to receive ultrasonic waves emitted from an object under test,
    wherein the at least one air-coupled ultrasonic transducer is positioned on a first side of the object, and
    wherein the at least one receiver comprises a first receiver positioned on the first side of the object and a second receiver positioned on a second side of the object that is opposite to the first side of the object.

11. An ultrasonic system for nondestructive testing, comprising:
    at least one air-coupled ultrasonic transducer configured to emit primary ultrasound waves that: interfere with each other, generate a plurality of frequency harmonics in the air, and form ultrasound shock waves that modify an acoustic impedance of the air, wherein the primary ultrasound waves comprise at least two fundamental frequency components that are multiples of each other and emitted simultaneously in locked phase; and
    at least one receiver configured to receive ultrasonic waves emitted from an object under test, wherein the object comprises an air duct.

12. A method for nondestructive testing, comprising:
    generating, using an array of air-coupled ultrasonic transducers, a plurality of frequency harmonics in an interference field in the air, wherein the generating comprises modifying an acoustic impedance of the air by forming ultrasound shock waves;
    receiving ultrasonic waves reflected from and generated in an object under test, wherein the ultrasonic waves are reflected from and generated in the object due to the generating of the plurality of frequency harmonics; and analyzing, using a computing device, signals indicative of the ultrasonic waves in the time domain, frequency domain, or both to determine at least one property of the object.

13. The method of claim 12, wherein generating the plurality of frequency harmonics in the interference field in the air comprises emitting primary ultrasound waves that interfere with each other, wherein the primary ultrasound waves comprises at least two fundamental frequency components that are multiples of each other and superimposed.

14. The method of claim 12, further comprising adjusting a position of the interference field.

15. The method of claim 12, further comprising positioning the array of air-coupled ultrasonic transducers within a predetermined distance of the object.

16. The method of claim 12, wherein receiving the ultrasonic waves comprises receiving ultrasonic waves from at least one non-contact air-coupled receiver positioned within a predetermined distance of the object.

17. A method comprising:
generating, using at least one air-coupled ultrasonic transducer, a plurality of frequency harmonics in an interference field in the air, wherein the generating comprises modifying an acoustic impedance of the air by forming ultrasound shock waves, wherein the at least one air-coupled ultrasonic transducer is positioned within a predetermined distance of an air duct;

receiving from at least one non-contact air-coupled receiver, ultrasonic waves generated in the air duct, wherein the ultrasonic waves are generated in the air duct due to the generating of the plurality of frequency harmonics; and analyzing, using a computing device, signals indicative of the ultrasonic waves to determine a flow rate of a fluid through the air duct.

18. The method of claim 17, wherein generating the plurality of frequency harmonics in the interference field in the air comprises emitting primary ultrasound waves that interfere with each other, wherein the primary ultrasound waves comprises at least two fundamental frequency components that are multiples of each other and superimposed.

* * * * *